United States Patent [19]

Berger et al.

[11] 4,099,883
[45] Jul. 11, 1978

[54] SULFUR DETECTING APPARATUS COMPRISING HOLMIUM, AND ERBIUM FILTERS

[76] Inventors: Abraham William Berger, 17 Westbourne Rd., Newton, Mass. 02159; Harry Eugene Stubbs, P.O. Box 686, Boston, Mass. 02102

[21] Appl. No.: 765,950

[22] Filed: Feb. 7, 1977

[51] Int. Cl.² .................. G01N 3/48; G02B 5/22; G02B 5/20
[52] U.S. Cl. .................................... 356/187; 350/313; 252/300
[58] Field of Search ............... 356/187, 188; 350/311, 350/313; 252/300

[56] References Cited

U.S. PATENT DOCUMENTS

| | | | |
|---|---|---|---|
| 3,489,498 | 1/1970 | Brody et al. | 356/187 |
| 3,877,819 | 4/1975 | Haas | 356/187 |

*Primary Examiner*—Vincent P. McGraw
*Assistant Examiner*—Rodney B. Bovernick

[57] ABSTRACT

An improvement in sulfur detecting apparatus is described wherein a filter system provides a signal path for light passing to detecting means, which signal path contains holmium and erbium, in quantities selected so that the optical transmission in the signal path is preponderantly in a wavelength interval 5 nm. wide and including the wavelength 374 nm. Embodiments of the invention additionally feature a calibration path for light passing to the light detecting means, containing samarium and holmium, the quantities of holmium and samarium being selected so that the optical transmission in the calibration path is preponderantly in a wavelenth interval 10 nm. wide and including the wavelength 374, the transmission being greater at wavelengths of 372 nm. and 378 nm. than at 374 nm. Further features includes a balanced transmission in the signal and calibration paths.

4 Claims, 5 Drawing Figures

SULFUR DETECTING APPARATUS COMPRISING HOLMIUM, AND ERBIUM FILTERS

BACKGROUND OF THE INVENTION

This invention relates to sulfur detecting apparatus. When sulfur in some form such as sulfur dioxide is introduced into a hydrogen-air flame, it forms molecular sulfur, $S_2$, which is excited and emits characteristic light in a series of bands in the blue and ultra violet region of the spectrum. In particular there are bands with wavelengths centered at about 364 nm., 374 nm., and 384 nm. At intermediate wavelengths near 370 nm. and 380 nm. there is little or no emission by the sulfur. The sulfur generated light is emitted diffusely from an extended volume around the flame rather than from a concentrated source. There is in addition to the sulfur emission a general flame background light emission which is independent of the presence of sulfur.

Optical band pass filters have been placed in the path of the light passing from the flame to a light detector to restrict the wavelengths to those of the sulfur generated light, minimize the background light passing to the detector, and so improve detection. Interference filters have been used since they are readily available with a narrow band pass. Interference filters have been unsatisfactory for this purpose, however, since the extended sulfur emitting volume around the flame provides light that is not practical to collimate while an interference type filter requires collimated light for proper operation. The alternative of using absorption type filters which are not sensitive to light direction is also unsatisfactory because known absorption filters have not had a narrow enough pass band to be useful.

SUMMARY OF THE INVENTION

We have discovered that the rare earths holmium and erbium can be used to produce optical filters of the absorption type operating satisfactorily in uncollimated light and having a narrow transmission band pass having a maximum at the sulfur emission at 374 nm. We have further discovered that the rare earths holmium and samarium can be used to produce optical filters of the absorption type operating satisfactorily in uncollimated light and having a transmission band with a minimum at the wave length of sulfur emission and maxima at either side of the wavelength of sulfur emission.

The invention features in sulfur detecting apparatus wherein a sample is excited to emit light and having, light detecting means arranged to receive the light, and an optical filter system positioned to filter the light passing to the light detecting means, the improvement wherein the filter system provides a signal path for light passing to the detecting means, which signal path contains holmium and erbium, in quantities selected so that the optical transmission in the signal path is preponderantly in a wavelength interval 5 nm. wide and including the wavelength 374 nm. Embodiments of the invention additionally feature a calibration path for light passing to the light detecting means, containing samarium and holmium, the quantities of holmium and samarium being selected so that the optical transmission in the calibration path is preponderantly in a wavelength interval 10 nm. wide and including the wavelength 374, the transmission being greater at wavelengths of 372 nm. and 378 nm. than at 374 nm. Further features include a balanced transmission in the signal and calibration paths.

DESCRIPTION OF PREFERRED EMBODIMENT

Figure 1:
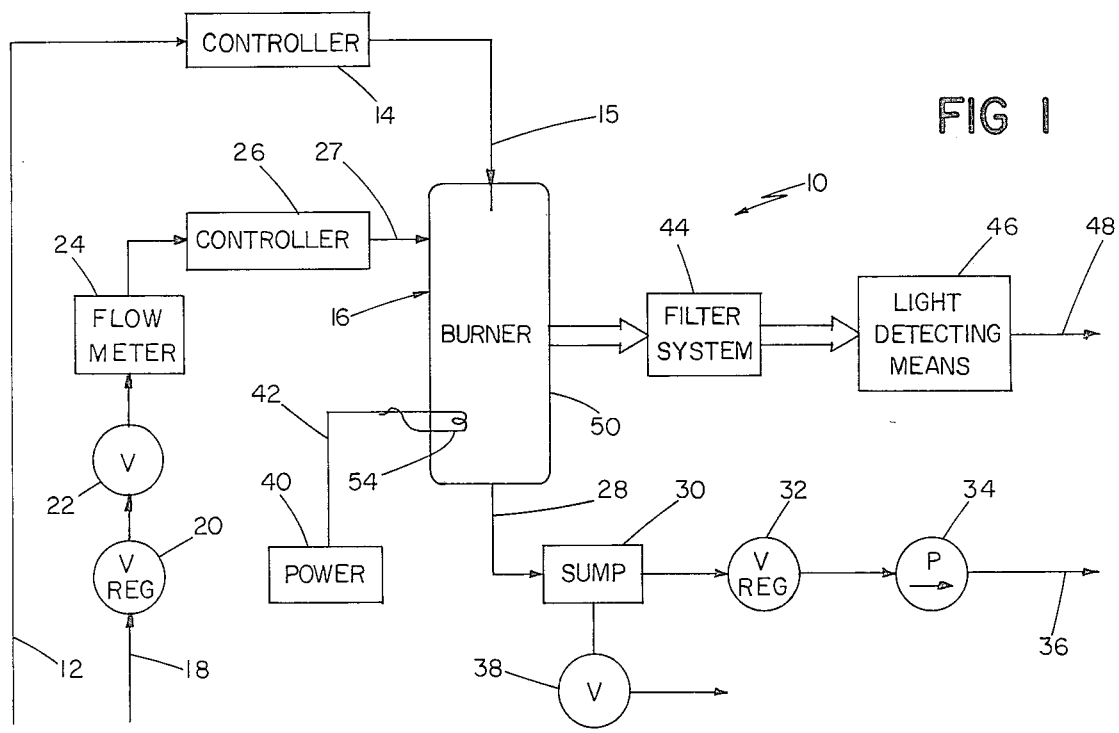
FIG. 1 shows in partially schematic form an instrument for detecting sulfur according to the invention.

The arrangement of an instrument 10 for detecting sulfur according to the invention can be understood with reference to FIG. 1. Inlet 12 admits a sample of air containing a small and unknown quantity of sulfur dioxide into instrument 10. Sample flow controller 14 is connected to receive sample from inlet 12 and discharge through burner inlet 15 into burner 16. Inlet 18 admits hydrogen into instrument 10. Pressure regulating valve 20 is connected to receive hydrogen from inlet 18. Shut off valve 22 is connected to receive effluent from valve 20. Flow meter 24 is connected to receive effluent from valve 22. Flow controller 26 is connected to receive effluent from meter 24 and discharge through burner entry 27 into burner 16. Conduit 28 is connected to receive the effluent from burner 16 and discharge into sump 30. Pressure regulating valve 32 is connected to receive effluent from sump 30. Pump 36 is connected to receive the effluent from valve 32. The effluent from pump 34 is discharged to the atmosphere through exhaust 36. Drain valve 38 is connected to discharge condensate from the bottom of sump 30. Igniter power supply 40 is connected to supply electrical power to burner 16 through leads 42. Optical filter system 44 is positioned to receive light issuing from burner 16. Light detecting means 46 is positioned to receive light passing through filter system 46. Electrical output lead 48 is connected to light detecting means 46 to transmit the output therefrom. Igniter filament 54, connected to leads 42, is sealed into the lower portion of envelope 50, and burner effluent conduit 28 is sealed to the bottom of envelope 50. When the instrument is in operation, inlet 15 acts as a flame holder, holding a flame for exciting sulfur molecules and providing a source of radiation of wavelengths characteristic of sulfur.

Figure 2:
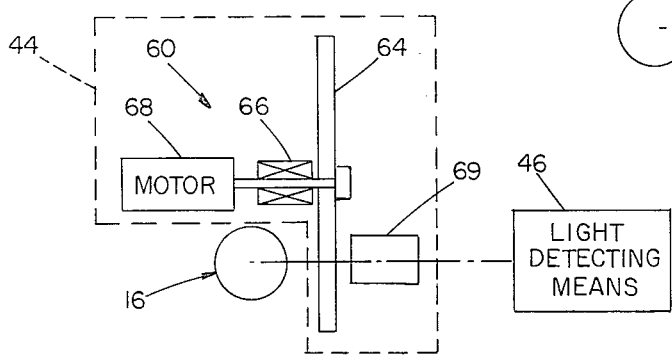
FIGS. 2, 3, and 4 show the details of the filter system of the instrument of FIG. 1.
Figure 3:
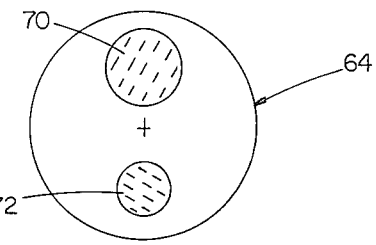
Figure 4:
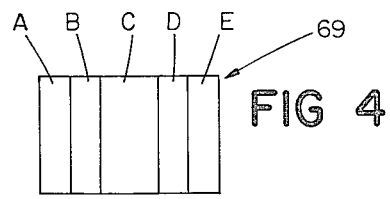

Optical filter system 44, shown more particularly in FIGS. 2, 3 and 4, is interposed between burner 16 and detecting means 46, and includes fixed filter element 69 and rotating filter wheel 64 supported on bearing 66 and driven by synchronous motor 68. Wheel 64 holds filter element 70 of a first type and filter element 72 of a second type as shown particularly in FIG. 3. The axis of filter wheel 64 is positioned so that, as the wheel rotates, filter elements 70 and 72 are successively interposed in the operative position between the burner and the light detecting means to provide alternative paths for light passing from burner 16 to detecting means 46. According to the invention, one of these alternative paths—namely, when filter element 70 is placed in the operative position—is a signal path selectively passing from burner 16 to responsive means 46 sulfur generated light of wavelength 374 nm. while selectively absorbing background light to nearby wavelengths. The second alternative path—namely, when filter element 72 is placed in the operative position—is a calibration path selectively absorbing sulfur generated light of wavelength 374 nm. while selectively passing from burner 16 background light at nearby wavelengths.

Filter element 69 is made up of several parts as shown particularly in FIG. 4. Parts A, B, D and E are glass filter elements available commercially. Identification and suitable suppliers are as follows:

| Element | Supplier | Thickness | Catalog Identification |
|---|---|---|---|
| A | PBL International Inc. Newburyport, Massachusetts | stock | GUV 36 |
| B | PBL International Inc. Newburyport, Massachusetts | stock | GUV 36 |
| D | PBL International Inc. Newburyport, Massachusetts | stock | GU 360 |
| E | Schott Optical Glass Inc. Duryea, Pennsylvania | 3 nm. | BG 38 |

Part C is a special glass 10 nm. thick containing holmium and having the following composition in weight percent.

$SiO_2$: 38.5
$B_2O_3$: 4.5
$Li_2O$: 0.5
$Na_2O$: 5.0
$K_2O$: 7.0
$BaO$: 8.0
$Al_2O_3$: 1.5
$La_2O_3$: 5.0
$HO_2O_3$: 30.0

Filter element 70 is a special glass of the following composition in weight percent:

$SiO_2$: 38.0
$B_2O_3$: 5.0
$Li_2O$: 0.5
$Na_2O$: 5.0
$K_2O$: 7.0
$BaO$: 22.0
$Al_2O_3$: 1.5
$La_2O_3$: 19.0
$Er_2O_3$: 2.0

Filter element 72 is a special glass of the following composition in weight percent:

$SiO_2$: 38.5
$B_2O_3$: 4.5
$Li_2O$: 0.5
$Na_2O$: 5.0
$K_2O$: 7.0
$BaO$: 13.0
$Al_2O_3$: 1.5
$La_2O_3$: 10.0
$Sm_2O_3$: 20.0

When filter element 70 is in the operative position, to provide the signal path, the optical transmission to the detector is restricted to a very narrow spectral band of about 5 nm. including with a maximum near the sulfur emission at 374 nm. and with half maximum points at about 371 nm. and 376 nm. The contribution of the several filter parts is as follows. Filter parts A, B, D and E taken together define a rather broad spectral transmission band including the general range of wavelengths when the sulfur emissions occur. The holmium containing glass (part C) and the erbium containing glass (element 70) then absorb light in parts of this general range to restrict the transmission to the very narrow band as stated.

When filter element 72 is rotated into the operative position to provide the calibration path, it forms, in cooperation with element 69, a transmission band with an overall wavelength interval of about 10 nm. but having a dip in the transmission in the middle of the range at about 374 nm. The calibration path therefore selectively absorbs the sulfur light of wavelength 374 nm. while passing background light of slightly different wavelength. As with the signal path, the filter elements A, B, D and E together define a broad transmission band. The part C of element 69 containing holmium and element 72 containing samarium then define the detailed shape of the transmission within the broad band to provide the result as stated.

Light detecting means 46 advantageously includes a photomultiplier operating into a synchronous detector synchronized to the rotation of filter wheel 64. These devices are well-known and need not be further discussed here.

The operation of the apparatus is as follows. Pump 34 is placed in operation and draws sample, which may be ambient air containing an unknown amount of sulfur dioxide, into inlet 12, thence through flow controller 14, and burner inlet 15 into burner 16. Power supply 40 is energized and supplies power to filament 54, which becomes hot. Valve 22 is then opened and hydrogen is drawn from some convenient source connected to inlet 18 into burner 16 through regulating valve 20, shut-off valve 22, flow meter 24, and flow controller 26. The effluent from burner 16 is drawn by the action of pump 34 into sump 30, thence through regulating valve 32, and discharged through exhaust 36. The flow controllers and regulating valves are adjusted to admit hydrogen in excess of the stoichiometric requirement for reaction with the oxygen in the admitted sample, and maintain steady flow through the apparatus. Suitable flow rates are 100 cc/min. of sample air and 150 cc/min. of hydrogen. When the hydrogen is first admitted it is ignited by hot filament 54, and thereafter a steady, hydrogen-rich flame is maintained.

The chemical reactions which take place in a flame are complex and incompletely known, but it is known that some or all of the sulfur dioxide admitted to the apparatus under the conditions described above reacts to form molecular sulfur, $S_2$, which is excited and radiates as described above. In addition to the light from sulfur, the combustion of the hydrogen and oxygen in the flame produces a background light which may be augmented by radiation generated by other materials that may be present in the sample.

The light from burner 16 passes through filter system 44 to light detector 46. As wheel 64 rotates the light will reach the detector 46 alternatingly by the signal path and by the calibration path depending on whether filter element 70 or element 72 is in the operative position. The synchronous detector will respond to the difference between the light transmitted along these two paths. Advantageously, in a calibration procedure when no sulfur is present in the gases admitted to the burner so that only background light is emitted, the two paths should be balanced so that equal quantities of light reach the detector by the two paths. This may conveniently be done by adjusting the aperture of one of filter elements 70 or 72 with a mask or even by black paint. The detector will then have zero output. When sulfur is then admitted to the burner it will emit light which will be transmitted in greater degree through the signal path than through the calibration path and the detector will respond accordingly to indicate the quantity of sulfur.

Figure 5:
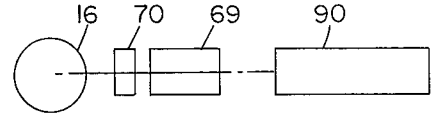
FIG. 5 shows an alternative embodiment of the invention

An alternative embodiment of the invention somewhat simpler than that described above is shown in FIG. 5. In this embodiment the rotating wheel is dispensed with and filter element 70 is fixed in the light path to the detector along with filter element 69 to provide a signal path. With the same optical properties as described above. For this embodiment light detecting means 90 is advantageously a photomultiplier operating into a d.c. amplifier.

What is claimed is:

1. In sulfur detecting apparatus wherein a sample is excited to emit light and having light detecting means arranged to receive said light, and an optical filter system positioned to filter said light passing to said light detecting means, the improvement wherein said filter system provides a signal path for light passing to said detecting means, said signal path containing holmium and erbium, the quantities of holmium and erbium in said signal path being selected so that the optical transmission in said signal path is preponderantly in a wavelength interval 5 nm wide and including the wavelength 374 nm.

2. Apparatus as claimed in claim 1 wherein said filter system additionally provides a calibration path for light passing to said light detecting means, said calibration path containing samarium and holmium, the quantities of holmium and samarium being selected so that the optical transmission in said calibration path is preponderantly in a wavelength interval 10 nm wide and including the wavelength 374, the transmission being greater at wavelengths of 372 nm and 378 nm than at 374 nm.

3. Apparatus as claimed in claim 2 wherein said signal and calibration paths are balanced so that light transmitted along them is equal when said sample is without sulfur.

4. Apparatus as claimed in claim 1 wherein the optical transmission in said signal path is less at wavelengths of 371 nm and 376 nm than at a wavelength of 374 nm.

* * * * *